(12) United States Patent
Shone et al.

(10) Patent No.: US 7,670,796 B2
(45) Date of Patent: Mar. 2, 2010

(54) METALLOPROTEASE ASSAY

(75) Inventors: Clifford Charles Shone, Salisbury (GB); Elizabeth R. Evans, Salisbury (GB); Stephen Peter Kidd, Salisbury (GB)

(73) Assignee: Health Protection Agency, Wiltshire, Great Britain (GB)

( * ) Notice: Subject to any disclaimer, the term of this patent is extended or adjusted under 35 U.S.C. 154(b) by 604 days.

(21) Appl. No.: 10/557,717

(22) PCT Filed: May 24, 2004

(86) PCT No.: PCT/GB2004/002233

§ 371 (c)(1),
(2), (4) Date: Mar. 7, 2007

(87) PCT Pub. No.: WO2004/104219

PCT Pub. Date: Dec. 2, 2004

(65) Prior Publication Data
US 2007/0148694 A1 Jun. 28, 2007

(30) Foreign Application Priority Data
May 23, 2003 (GB) ................................. 0311961.7

(51) Int. Cl.
*C12Q 1/37* (2006.01)
(52) U.S. Cl. ......................................... 435/23; 435/7.4
(58) Field of Classification Search .................. 435/23, 435/7.1, 7.4, 7.5
See application file for complete search history.

(56) References Cited

U.S. PATENT DOCUMENTS

| 5,856,082 A | 1/1999 | Aebersold et al. |
| 6,337,386 B1 * | 1/2002 | Shone et al. ................. 530/329 |
| 2003/0054426 A1 | 3/2003 | Welsch et al. |

FOREIGN PATENT DOCUMENTS

| DE | 19831110 | 1/2000 |
| WO | 95/33850 | 12/1995 |
| WO | 00/11208 | 3/2000 |
| WO | 00/48004 | 8/2000 |
| WO | 03/001206 | 1/2003 |

OTHER PUBLICATIONS

Cummings, R.T., et al., "A peptide-based fluorescence resonance energy transfer assay for *Bacillus anthracis* lethal factor protease"., PNAS, vol. 99, No. 10, pp. 6603-6606, (2002).

Hallis, B., et al., "Development of novel assays for botulinum type A and B neurotoxins based on their endopeptidase activities"., Journal of Clinical Microbiology, vol. 34, No. 8, pp. 1934-1938, (1996).

International Search Report dated Oct. 13, 2004 for corresponding PCT application No. PCT/GB2004/002233.

Koopmann, J-O., et al., "High affinity capture surface for matrix-assisted laser desorption/ionisation compatible protein microarrays"., Rapid Communications in Mass Spectrometry, vol. 17, pp. 455-462, (2003).

Lapolla, A., et al., "Advanced glycation end products: a highly complex set of biologically relevant compounds detected by mass spectrometry"., Journal of Mass Spectrometry, vol. 36, pp. 370-378, (2001).

Loew, D., et al., "Proteolysis of the exodomain of recombinant protease-activated receptors: Prediction of receptor activation or inactivation by MALDI mass spectrometry"., Biochemistry, vol. 39, No. 35, pp. 10812-10822, (2000).

Min, D-H., et al., "Chemical screening by mass spectrometry to identify inhibitors of anthrax lethal factor"., Nature Biotechnology, vol. 22, No. 6, pp. 717-723, (2004).

Mock, M., et al., "Progress in rapid screening of *Bacillus anthracis* lethal factor activity"., PNAS, vol. 99, No. 10, pp. 6527-6529, (2002).

Parker, C.E., et al., "Monitoring cleavage of fusion proteins by matrix-assisted laser desorption Ionization/mass spectrometry: Recombinant HIV-1$_{IIIB}$ p26"., Analytical Biochemistry, vol. 239, No. 0286, pp. 25-34, (1996).

She, Y-M., et al., "Determination of the complete amino acid sequence for the coat protein of brome mosaic virus by time-of-flight mass spectrometry"., The Journal of Biological Chemistry, vol. 276, No. 23, pp. 20039-20047, (2001).

Trummal, K., et al., "MALDI-TOF mass spectrometry analysis of substrate specificity of lebetase, a direct-acting fibrinolytic metalloproteinase from *Vipera lebetina* snake venom"., Biochimica et Biophysica Acta, vol. 1476, pp. 331-336, (2000).

U.K. Search Report dated Sep. 15, 2003 for application No. GB 0311961.7.

Yao, Z-P., et al., "Mass spectrometry based proteolytic mapping for rapid virus identification"., Analytical Chemistry, vol. 74, No. 11, pp. 2529-2534, (2002).

Yokoyama, R., et al., "Measurement of aspartyl aminopeptidase activity by matrix-assisted laser desorption/Ionization time-of-flight mass spectrometry"., Analytical Sciences, vol. 17 supplement, pp. i1551-i1553, (2001).

* cited by examiner

*Primary Examiner*—Ralph Gitomer
(74) *Attorney, Agent, or Firm*—Evan Law Group LLC

(57) ABSTRACT

An assay to detect a metalloprotease in a sample, comprising contacting the sample with a substrate. The metalloprotease reacts with the substrate to form a product comprising a tag. This is followed by selectively binding the tag to a solid phase, wherein the solid phase comprises a binding partner for the tag. Measuring the mass of the product takes place to determine the presence of the metalloprotease in the sample.

20 Claims, 5 Drawing Sheets

| VAMP Product (approx MH+ 2411) | BoNT/B (ng) in Assay |
|---|---|
| | 0 |
| | 0.2 |
| | 0.67 |
| | 2.0 |
| | 6.7 |
| | 20 |

METALLOPROTEASE ASSAY

The invention relates to an assay for metalloproteases, especially for detecting the *botulinum* neurotoxins and anthrax lethal factor. The invention relates also to substrates for the assay.

Various strains of the bacterium *Clostridium botulinum* produce a family of seven structurally related but antigenically different protein neurotoxins (types A to G) which cause the syndrome botulism. Symptoms are presented as widespread flaccid paralysis which often results in death. Much effort has been imparted by the food industry to ensure that food treatment processes prevent the growth and toxin production of *C. botulinum* and there is a need for rapid, sensitive and specific assays for these toxins. At present the only method of confidence in the detection of the toxins is the acute toxicity test performed in mice. Although this test is exquisitely sensitive, with a detection limit of 1 mouse 50% lethal dose [$MLD_{50}$] being equivalent to 10-20 pg of neurotoxin/ml, it has a number of drawbacks: it is expensive to perform, requires a large number of animals and is not specific for the neurotoxin unless neutralisation tests using a specific antiserum are carried out in parallel. In addition the test takes up to 4 days to complete. The increasing resistance to such animal tests has also required the development of alternative rapid in vitro assays. A number of immunoassay systems have been reported but these immunoassays do not measure the biological activity of the neurotoxin and can lead to false positive results.

Over the past years significant progress has been made in deciphering the mode of action of the clostridial neurotoxins. The toxins have been demonstrated to act at the cellular level as highly specific zinc endoproteases cleaving various isoforms of three small proteins controlling the docking of the synaptic vesicles with the synaptic membrane. *Botulinum* neurotoxins A and E cleave specifically the 25 kDa synaptosomal associated protein (SNAP-25). *Botulinum* neurotoxin C cleaves the membrane protein syntaxin and SNAP-25. *Botulinum* neurotoxins types B, D, F and G act on a different intracellular target, vesicle-associated membrane protein (VAMP), also termed synaptobrevin. With the exception of *botulinum* type B and tetanus neurotoxins, all of the clostridial neurotoxins cleave their protein targets at different peptide bonds, generating fragments of different molecular sizes.

It is known from WO 95/33850 to immobilize a toxin substrate on a column, combine that with a solution suspected of containing toxin and then use antibodies specific to cleaved substrate to report presence of toxin. This assay works well, but requires specific reagents in the immobilized substrate and the detecting antibodies.

Anthrax lethal toxin, produced by the bacterium *Bacillus anthracis*, is the major cause of death in animals infected with anthrax. One component of this toxin, lethal factor (LF), is a metalloprotease which has been shown to cleave the amino terminus of mitogen-activated protein kinase kinases 1 and 2 (MAPKK1 and MAPKK2). This cleavage inactivates MAPKK1 and inhibits the MAPK signal transduction pathway. Presently, there is no efficient assay for this toxin.

An object of the present invention is to provide a further assay for metalloprotease, especially for the *botulinum* toxins and anthrax lethal factor. In preferred embodiments, objects of the invention include providing an improved assay and an assay which can be used to detect different metalloproteases simultaneously.

A first aspect of the invention provides an assay for a protease, especially a metalloprotease, comprising the following steps:
  (a) combining a test compound with a substrate which comprises (i) a cleavage site for the protease, wherein the protease cleaves the substrate to form a product, and (ii) optionally, a tag that enables binding of the product to a solid phase,
  (b) binding the product to a solid phase; and
  (c) determining the mass of the product by mass spectrometry.

An option is to use a substrate already bound to a solid phase, in which case step (b) is not needed as product (if any) will be bound to the solid phase.

In use of an embodiment of the invention for assay of metalloprotease toxin, substrates are used that are specifically cleaved at one site thus generating at least one product, a fragment of the substrate, of known molecular mass which may be used to identify the toxin serotype.

The assay system has the advantage that the serotype of a *botulinum* toxin may be determined by the mass of the fragment produced thus negating the need for specialised antibody reagents in the detection step. A further advantage of the invention is that it allows simultaneous assay of many, e.g. 4, 5, 6 or 7 serotypes of *botulinum* toxin. This is because substrates can be used such that the masses of the peptide fragments released are different for each of the *botulinum* neurotoxins.

Additionally, since the assay depends upon a highly conserved biological activity of the toxin, antigenic variations between toxins of the same group will not significantly affect the working of the assay. Further advantages of the assay system are that it is relatively rapid compared to ELISA systems, has a sensitivity better than conventional ELISA systems, and that only biologically active toxin is detected.

In a further embodiment of the invention, the assay comprises:
  (a) combining a test solution with substrate containing VAMP (synaptobrevin) and/or SNAP-25 and/or syntaxin (or fragments of these) to form a mixture,
  (b) incubating the mixture in a buffer,
  (c) binding the mixture on a solid-phase designed for mass spectrometry, and
  (d) detecting one or more cleavage products by mass spectrometry.

The invention may also be carried out by:
  combining a test solution with a substrate solution (containing derivatives of VAMP/synaptobrevin and/or SNAP-25 and/or syntaxin) in which the substrate has been modified with a tag for binding to a solid phase,
  incubating the mixture, e.g. in a suitable buffer system,
  binding the incubated mixture on a solid-phase, designed for mass spectrometry, in which components of the mixture are bound via the binding tag, and
  detecting and characterising one or more cleavage products by mass spectrometry The tag is used to bind substrate and/or product to a solid phase so that the mass of the substrate or product can be determined. In some cases, a suitable tag occurs naturally in the substrate, for example VAMP/synaptobrevin will bind to hydrophobic surfaces without the need to be modified. If the substrate does not already comprise a tag then one can be introduced into or attached to the substrate.

The tag enables selective binding of product to the solid phase, with the advantage that product is at least partially separated from other components of the mixture which might interfere with the mass measurement step. Assays of the invention thus preferably include a further step of washing the solid phase to remove unbound components.

After the substrate and test compound are combined, protease present in the test compound cleaves the substrate to form two or more, generally two, fragments. The measurement/detection step is designed to detect one of these, usually the smaller fragment, referred to as the product. Generally, before measuring whether product has been formed, the mixture is allowed to incubate for a period. This allows access of the protease to the substrate, enabling a signal to be obtained even for very low protease levels. A suitable incubation time varies according to the details of the assay, but incubation of at least 10 minutes is usual, and at least 30 minutes or at least an hour is preferred.

The solid phase is such that it can be used for measurement of mass of the product, suitably by the SELDI method though other methods are also of application to the invention. Generally, the solid phase comprises a metallic surface to which or on which product can be bound. The surface is typically derivatized to facilitate this binding, and one solid phase used in specific embodiments is a chip.

Product can be bound to the surface by merely allowing solution containing product to dry on the surface. Preferably, product is specifically bound to the surface and then washed with buffer and/or water. Washed product can then be treated, if necessary, so that it is no longer covalently bound to the surface. The mass of product is then determined.

VAMP/synaptobrevin is the native protein target for *botulinum* serotypes B, D, F and G and contains the sequence: tyrosine: tryptophan: tryptophan (YWW) in its C-terminal region, which sequence binds strongly to hydrophobic surfaces. The sequence thus provides a naturally occurring tag for binding peptide fragments to a hydrophobic chip surface designed for mass spectral analysis. A similar tag or motif is optionally incorporated into those toxins substrates (e.g. SNAP-25) where a similar hydrophobic domain is absent so as to provide a modified substrate comprising a site for cleavage by a protease and a domain for binding the modified substrate, whether intact or after cleavage by protease, to a hydrophobic surface.

A hydrophobic motif can be incorporated into or added to a given substrate by a short sequence of contiguous hydrophobic amino acids, e.g. leucine, isoleucine, valine, phenylalanine, tyrosine and tryptophan. A sequence of from 3 to 5 is generally suitable to enable the substrate (and fragment generated by cleavage) to bind to a hydrophobic surface without rendering the substrate or fragment insoluble.

Thus a further embodiment of the invention comprises:
  combining a test solution with a substrate solution (containing derivatives of VAMP/synaptobrevin and/or SNAP-25 and/or syntaxin) in which the substrate either contains a tag/motif for binding hydrophobic surfaces or has been modified to contain such a tag/motif,
  incubating the mixture in a suitable buffer system,
  binding the mixture on a hydrophobic solid-phase, designed for mass spectrometry, in which components of the mixture are bound via the binding hydrophobic tag/motif, and
  detection and characterisation of one or more cleavage products by mass spectrometry.

A further example of a tag for directed binding is biotin. A biotin tag may be introduced into a protein via cysteine residues. These may be either naturally occurring or introduced by mutagenesis. VAMP/synaptobrevin does not contain any cysteine residues in the C-terminal region and a cysteine may be added, by mutagenesis, to the C-terminus of the hydrophilic domain to give the C-terminal sequence:

lysine: asparagine: leucine: lysine: cysteine (KNLKC).

The latter sequence may then be conveniently modified to contain a biotin tag with chemical reagents such as polyethylene oxide maleimide-activated biotin.

In the case of SNAP-25, a number of cysteine residues exist in the peptide, but are not conveniently located. For efficient operation of the invention, it is preferred to modify these cysteines, by mutagenesis, into serine residues and also introduce an additional cysteine, e.g. at the C-terminus. The latter will then provide a suitable site for the incorporation of a biotin residue.

After cleavage of the biotinylated substrate by a toxin, the resulting biotinylated fragment may be immobilised onto a streptavidin-coated solid phase designed for mass spectral analysis. Hence, specific embodiments of the invention using biotin and streptavidin comprise:
  combining a test solution with a substrate solution (containing derivatives of VAMP/synaptobrevin and/or SNAP-25 and/or syntaxin) in which the substrate contains a biotin residue,
  incubating the mixture in a suitable buffer system,
  binding the mixture on a streptavidin-coated solid-phase, designed for mass spectrometry, in which components of the mixture are bound via the biotin residue, and
  detecting and characterising one or more cleavage products by mass spectrometry.

The assays can be carried out using a single substrate that is cleaved by different toxins/proteases, in or potentially in a test compound, to yield different products that are distinguishable from each other by their mass. The assays can also be carried out using a plurality of substrates cleaved by different toxins/proteases to yield different products. Hence, a single assay can identify presence of one or a plurality of toxins/proteases.

In an application in which the assay of the invention is used to detect toxin in a complex medium, such as a food stuff, it may be necessary to remove the bulk of the food stuff prior to assay using SELDI-MS. This may easily be achieved by introducing a pre-capture step as follows:
  mix the sample with a resin on which an antibody to the toxin has been immobilised
  remove the unbound material by washing
  elute the toxin using a low pH buffer (typically pH4 or less, preferably pH3 or less)
  test the elute for the presence of toxin using the assay of the invention.

Generally, the pre-capture comprises mixing the test compound with antibody specific for the toxin, separating the antibody from the mixture, thereby separating toxin, if present, from the mixture, to form a pre-capture mixture, and testing the latter for toxin. A similar procedure can be employed, if necessary, for other media such as serum and fecal samples.

Anthrax lethal factor cleaves a small peptide from the N-terminus of mitogen-activated kinase kinases 1 and 2 (MAPKK1 or MAPKK2). A peptide is cleaved from MAPKK2 with the sequence:
  Leucine-alanine-arginine-arginine-lysine-proline-valine-leucine-proline (LARRKPVLP).

MAPKK1 or MAPKK2, or a fragment thereof, may be modified for the assay of the invention by the addition of a cysteine residue, optionally to the N-terminus, by mutagenesis using a similar strategy described for SNAP-25 above. This residue may then be used as a site for the introduction of a biotin moiety.

In yet a further specific embodiment of the invention is an assay which may be used to detect the presence of anthrax lethal factor or anthrax lethal toxin and this comprises:

combining a test solution with a substrate comprising MAPKK1 or MAPKK1 (or fragments of these) and in which the substrate also contains a biotin residue, incubating the mixture in a suitable buffer system, binding the mixture on a streptavidin-coated solid-phase, designed for mass spectrometry, in which components of the mixture are bound via the biotin residue, and detecting and characterising one or more cleavage products by mass spectrometry.

For both *botulinum* toxin and anthrax lethal factor assays, it is straightforward to conceive of various other tags that are readily employed in the invention to capture a peptide fragment on the surface designed for mass spectral analysis. Examples of these include: a motif consisting of charged residues for capturing the peptide fragment on a cationic or anionic exchange matrix, and a motif that is recognised by an antibody immobilised on a chip surface.

One technique for coupling the test compound to the solid-phase is via an antibody. This can be an antibody which recognises a specific sequence on the peptide substrate, e.g. the C-terminal sequence of VAMP: tryptophan: tryptophan: lysine: asparagine: leucine: lysine (WWKNLK)

More preferably, the antibody will recognise a newly exposed N- or C-terminal sequence on the substrate which results from the proteolytic action of the neurotoxin. These antibodies more preferably bind to product but not to substrate, improving the selective binding of product to the solid phase.

For example, in the case of type B neurotoxin, the toxin cleaves between a glutamine and a phenylalanine bond of VAMP resulting in the newly exposed peptides sequences:

KAASSEF-n terminal and LQAGASQ-c terminal.

Antibodies raised against these peptides may be used as the solid phase capture in the assay of the invention. These antibodies may be polyclonal, e.g. raised in rabbits, but are preferably monoclonal, such as mouse monoclonal antibodies.

For the assay of the various *botulinum* serotypes and anthrax LF, antibodies are suitably produced against the following sequences:

| | | |
|---|---|---|
| BoNT/A | 1. | RIDEANQ-c terminal |
| | 2. | GLMKTAR-n-terminal |
| BoNT/B | 1. | KAASSEF-n terminal |
| | 2. | LQAGASQ-c terminal |
| BoNT/C | 1. | IDEANQR-c terminal |
| | 2. | SGLMKTA-n terminal |
| BoNT/D | 1. | VLERDQK-c terminal |
| | 2. | RDDLESL-n terminal |
| BoNT/E | 1. | QNRQIDR-c terminal |
| | 2. | SDAKEMI-n terminal |
| BoNT/F | 1. | KVLERDQ-c terminal |
| | 2. | DDLESLK-n terminal |
| BoNT/G | 1. | SQFESSA-c terminal |
| | 2. | YKRKLKA-n terminal |
| Anthrax LF | 1. | RRKPVLP-c terminal |

(note that the above sequences are generated by cleavage of the toxin substrate and hence the cleavage site is between the respective c-terminal and n-terminal ends of the pairs; the cleavage site for tetanus toxin is the same as for BoNT/B).

Antibodies may be made by (i) adding a cysteine residue to the left-hand side of the above sequences, (ii) coupling to a suitable carrier protein, and (iii) immunisation of the animal of choice.

An advantage of using antibodies to the above peptides in the assay system is that the cleavage product will be selectively bound. A further and significant advantage is that it does not matter if there is a small amount of the intact substrate that also binds, since the mass spectral analysis can be made selective for peptides of a defined size so that the intact substrate will not interfere with the detection process.

Thus, a further embodiment of the invention comprises:

combining a test solution with a substrate to form a mixture, optionally, incubating the mixture in a suitable buffer system, binding the mixture on an antibody-coated solid-phase, designed for mass spectrometry, and detection and characterisation of one or more cleavage products by mass spectrometry.

A number of abbreviations are used herein. "SELDI-MS" means "surface-enhanced laser desorption/ionization time-of-flight mass spectrometry". "BoNT" means *botulinum* neurotoxin which can be one of 7 serotypes labelled A-G. For example BoNT/A means *botulinum* neurotoxin serotype A. "VAMP" or "VAMP/synaptobrevin" means "vesicle-associated membrane protein" which is a protein substrate for BoNT/B, BoNT/D, BoNT/F and BoNT/G. "SNAP-25" means "synaptosomal protein of 25 kilodaltons" which is a substrate for BoNT/A, BoNT/C and BoNT/E. "MAPKK" means "mitogen-activated protein kinase kinase" and is a substrate for anthrax lethal factor.

The invention has been described in relation to detection of metalloprotease toxins. In a more general aspect, the invention relates to detection of proteases, providing an assay comprising:

combining a test compound with a substrate, wherein the protease reacts with the substrate to form a product; and detecting presence of the protease by measuring the mass of the product.

Typically, the protease cleaves the substrate so as to form a product having lower mass than the substrate, and presence of the protease is detected by measuring the mass of the product.

The invention relates also to reagents and specifically provides a reagent comprising the substrate and the tag of the invention and, separately, a solid phase component comprising the substrate and a solid phase for mass determination in a mass spectrometer.

The invention is now described in the following examples with reference to the accompanying drawings in which:

FIG. 1 shows the results of a SELDI MS assay for BoNT/B in which recombinant VAMP (excluding the transmembrane domain) was used as the substrate for BoNT/B and the C-terminal fragment of VAMP was captured on a hydrophobic (H4) chip using the native YWW motif on VAMP;

FIG. 2 shows the results of a SELDI MS assay for BoNT/B in which a VAMP (60-94) peptide was used as the substrate for BoNT/B and the C-terminal fragment of VAMP was captured on a hydrophobic (H4) chip using the native YWW motif on VAMP;

Figure 4:
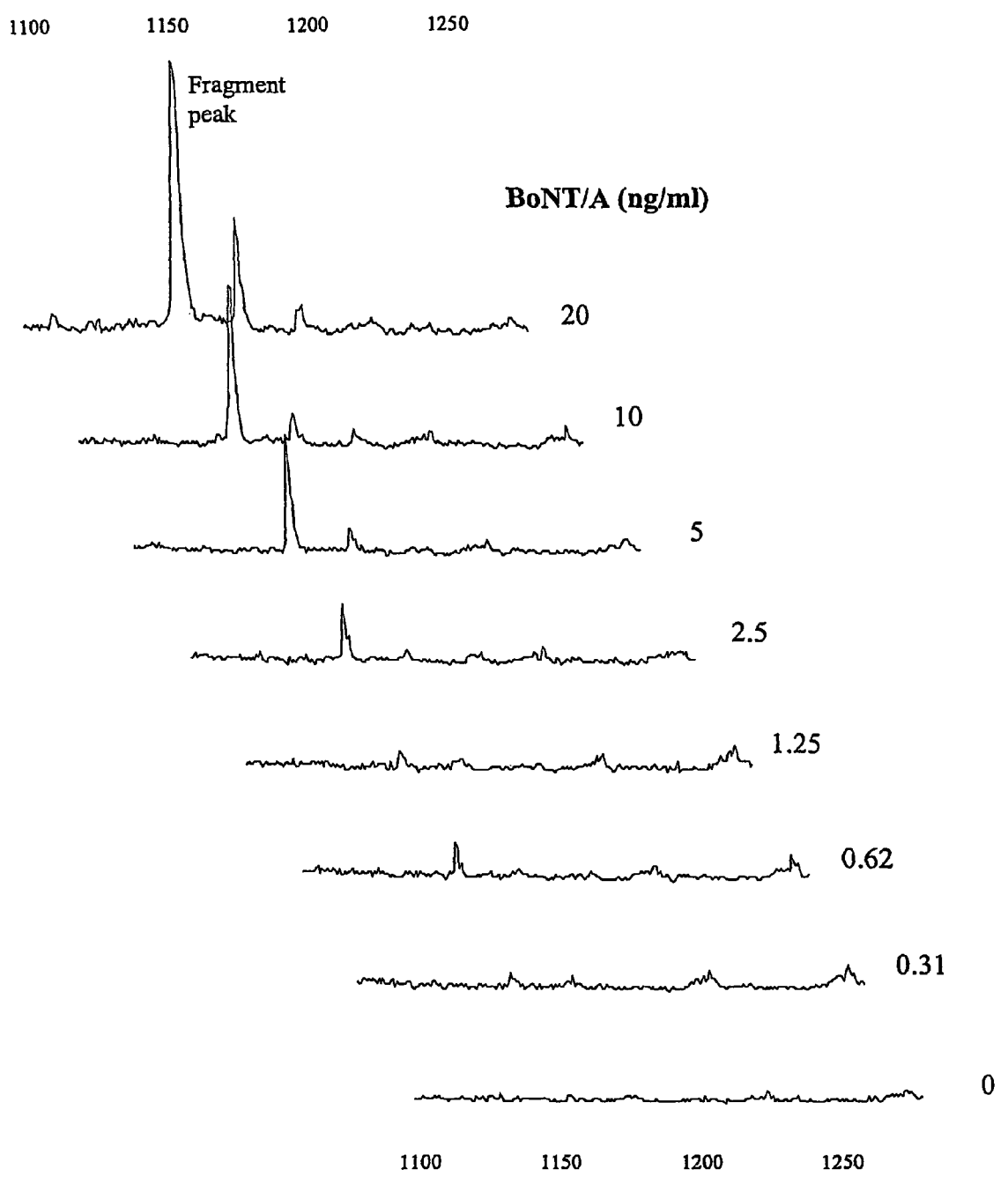
Figure 5:
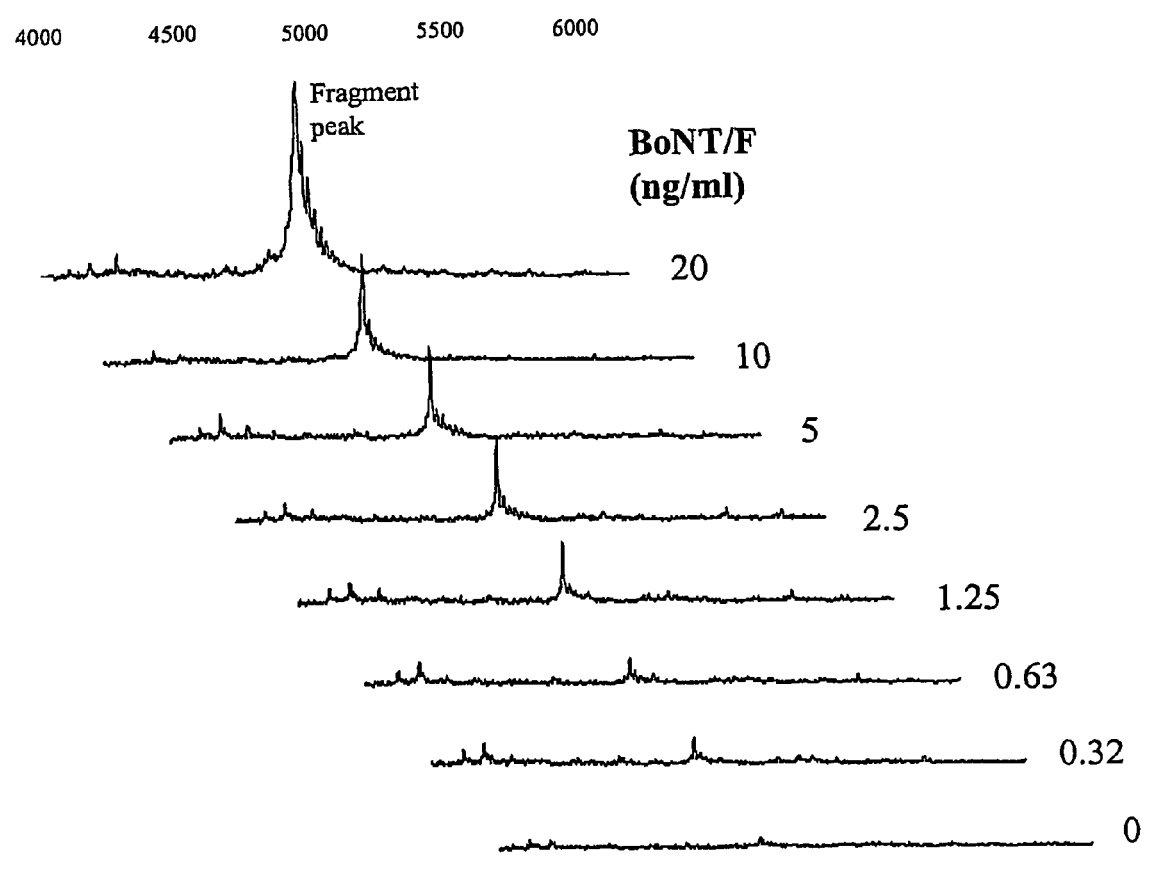
Figure 3:
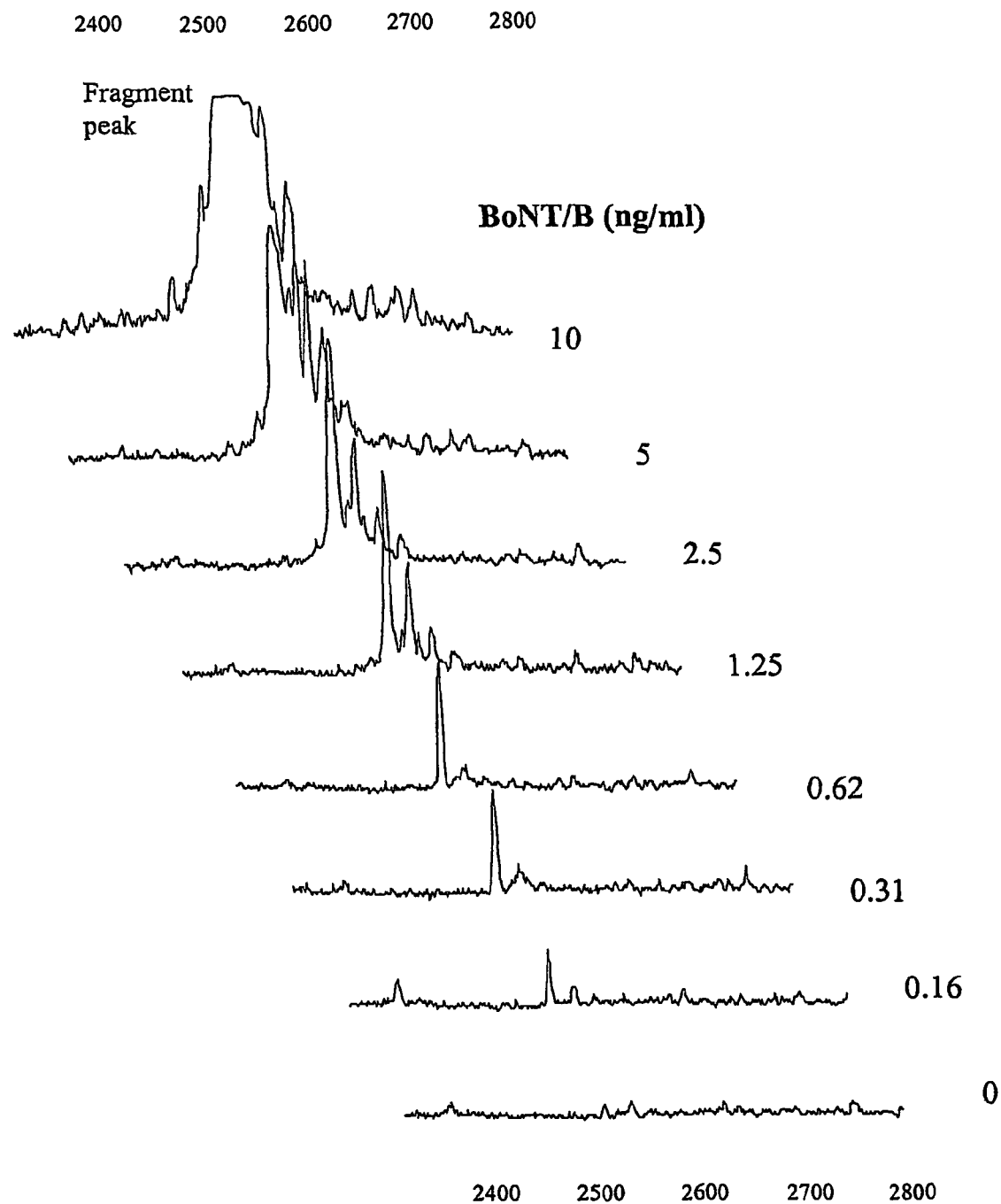
FIG. 3 shows the results of a SELDI MS assay for BoNT/B in which a VAMP (60-94) peptide which had a biotin residue at the C-terminus was used as the substrate for BoNT/B and the C-terminal fragment of VAMP was captured using a streptavidin-coated PS20 chip.

FIG. 4 shows the results of a SELDI MS assay for BoNT/A using recombinant SNAP-25 in which a C-terminal hydrophobic motif (sequence: YWW) had been added and the C-terminal fragment of SNAP-25 containing the YWW sequence was captured on a hydrophobic (H4) chip; and FIG. 5 shows the results of a SELDI MS assay for BoNT/F in which recombinant VAMP (excluding the transmembrane domain) was used as the substrate for BoNT/F and the C-terminal fragment of VAMP was captured on a hydrophobic (H4) chip using the native YWW motif on VAMP.

EXAMPLES

Example 1

Production of Recombinant Substrates for the Assay System

Standard molecular biology protocols were used for all genetic manipulations (eg. Sambrook et al. 1989, Molecular Cloning a Laboratory Manual, Second Edition, Cold Spring Harbor Laboratory Press, Cold Spring Harbor, N.Y.).

VAMP constructs were prepared using the Polymerase Chain Reaction (PCR) to amplify the required regions of human VAMP Isoform-1. Standard molecular biology techniques were used to add any additional amino acid residues required. Examples of these include:

VAMP amino acids 1-96
VAMP amino acids 1-96 with an additional C-terminal cysteine residue.

For these VAMP constructs, oligonucleotides were modified by PCR to introduce BamH1 and XhoI sites at the 5' and 3' ends respectively. A truncated gene with the same cloning sites but lacking the 3' sequence encoding a hydrophobic tail was also prepared by PCR. The gene fragments were subcloned into the expression vector pGEX-4T1 (AP Biotech) digested with BamHI-XhoI. All clones were checked by sequencing to confirm the insertion of the correct fragment. The clones were transformed into the BL21 expression strain (Promega UK) before expression and purification. Cultures of BL21::pGEX 4T-VAMP were grown in Terrific Broth and production of the GST-VAMP fusion protein induced with 500 µM IPTG. Cells were harvested by centrifugation and the pellet resuspend pellet in 40 ml PBS (pH 7.4) and stored at −20° C. until use. Cells (20 ml) were disrupted by sonication and then centrifuged at 15,000 rpm for 30 minutes. The supernatant was diluted with 20 ml of PBS and applied slowly (4-5 ml/min) to a column (5 ml) of Glutathione Sepharose GSTrap FF column (AP Biotech) which had previously been equilibrated with 5 column volumes of PBS. The column was washed with 10 column volumes of PBS and the bound GST-VAMP eluted slowly in 5 column volumes of 50 mM Tris, 10 mM reduced glutathione; pH 8.0 (4-5 ml-min). Fractions containing GST-VAMP were dialysed against either 50 mM HEPES (pH 7.4), or PBS if the construct is to be biotinylated.

SNAP-25 constructs were prepared using the Polymerase Chain Reaction (PCR) to amplify the required regions of human SNAP-25. Standard molecular biology techniques were used to add or modify any amino acid residues as required. Examples of these include:

SNAP-25 amino acids 1-206;
SNAP-25 amino acids 1-206 in which the 4 internal cysteine residues have been mutated to serine; and
SNAP-25 amino acids 1-206 in which the 4 internal cysteine residues have been mutated to serine and which has an additional C-terminal cysteine residue added to the C-terminus.

For these SNAP-25 constructs, oligonucleotides were modified by PCR to introduce BamH1 and EcoR1 sites at the 5' and 3' ends respectively. Expression and purification was as described for the VAMP constructs above.

Example 2

Biotinylation of Substrates for the Assay

Polyethylene oxide-maleimide activated biotin (Pierce) at 10 mM was freshly prepared in PBS. To 100 µl of this biotin solution, 2.5 ml of approximately 1 mg/ml GST-VAMP, GST-SNAP-25 or MAP kinase kinase peptide in PBS was added and incubated at room temperature for 4 hours. In all instances the substrate contained a free cysteine residue. Remaining free biotin was then removed by dialysis or chromatography into 50 mM Hepes (pH 7.4) buffer.

Example 3

Assay for *botulinum* Neurotoxin

Types B, D, F and G Using a Hydrophobic Chip

The assay used VAMP construct which consists of GST Human-VAMP-1 (ending in KNLK) 5 mg/ml in Hepes (50 mM, pH 7.4). This was diluted with an equal volume of Hepes (50 mM, pH 7.4) buffer containing 50 mM DTT and 50 µM $ZnCl_2$. To 3 µl of the above substrate solution add 12 µl of toxin solution in a buffer such as Hepes (50 mM, pH 7.4) and incubate the mixture for 2 hours at 37° C.

Standard toxin solutions were prepared in order to calibrate the assay system. Dilutions of: 0.1, 0.03, 0.01, 0.003, 0.001, 0.0003, 0 µg/ml were prepared in a suitable buffer such as Hepes (50 mM, pH 7.4). These were mixed and incubated with the VAMP substrate as described above.

Spots on a H4 (hydrophobic) chip (Ciphergen Inc.) were outlined with a wax pen and washed with 10 ul water per spot. After incubation, 3 µl of each test samples was then added to each spot and incubated for 30 min at RT. Spots were then washed with 10 µl Hepes and 10 µl water. After washing, chips were then air-dried and 2×0.5 µl Energy Absorbing Molecules (alphacyano-4-hydroxy cinnamic acid diluted in 50% acetonitrile and 0.5% trifluroacetic acid to ⅓ saturation) was added and dried.

Chips were then read in a SELDI mass spectrometer (Ciphergen Inc.) Depending on the *botulinum* serotype present, peaks of various masses will be present in the mass spectrum. Approximate masses of the expected peaks are shown below:

peptide product mass for BoNT/B=2411.3
peptide product mass for BoNT/F=4280.3
peptide product mass for BoNT/D=4152.2
peptide product mass for BoNT/G=1762.1

The mass of the peak observed in the spectrum thus confirms and identifies the *botulinum* toxin serotypes present in test samples.

Figure 2:
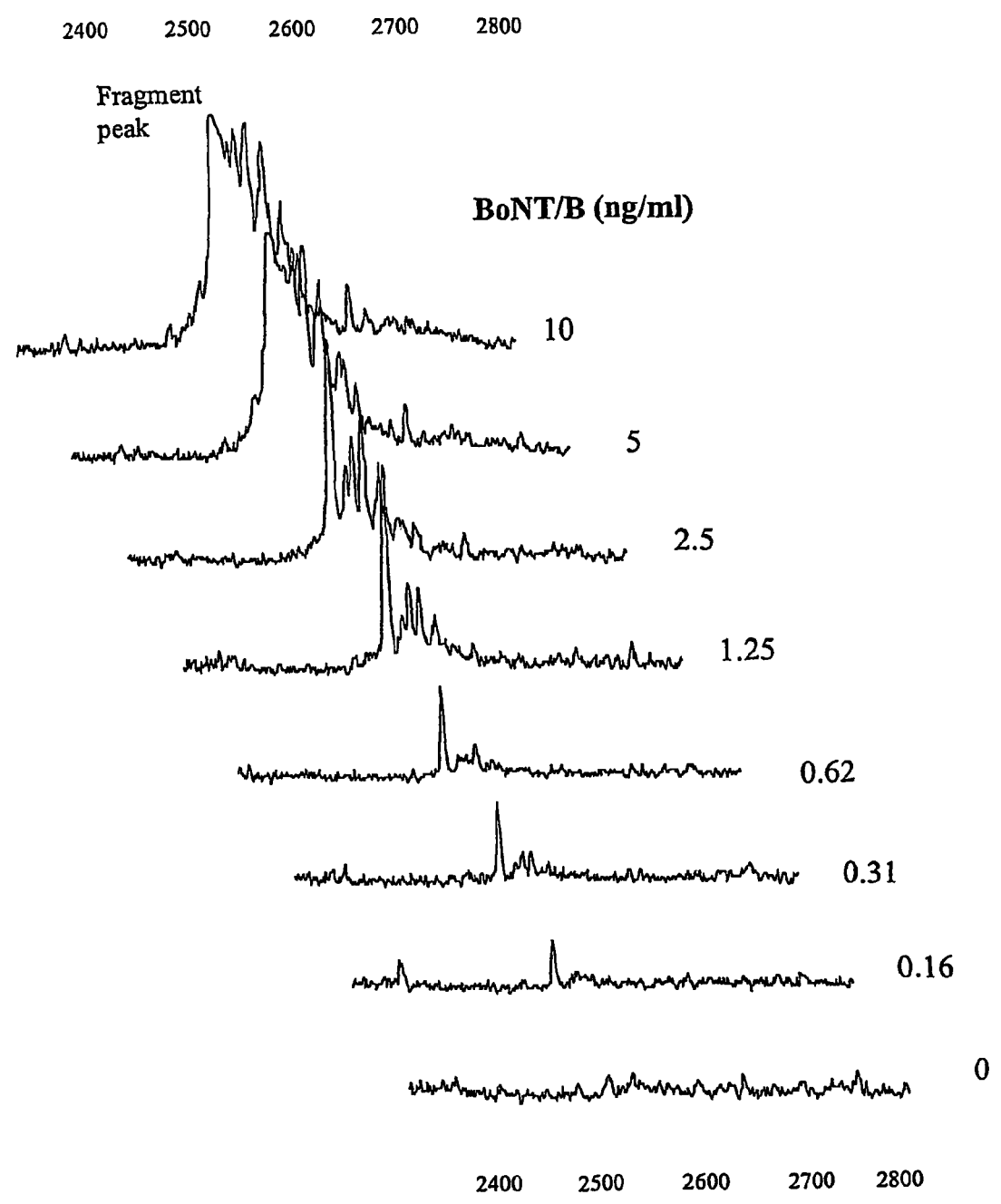

An assay for BoNT/B was carried out on a Ciphergen H4 hydrophobic chip as described using known toxin concentrations. The strong mass peak at approx. $MH^+$ 2411 indicated the presence of BoNT/B—see the results illustrated in FIG. 1. A further assay using a VAMP (60-94) peptide was tested using an H4 chip and the results are shown in FIG. 2. An assay for BoNT/F was tested and the results are shown in FIG. 5.

Example 4

Assay for *botulinum* Neurotoxin

Types B, D, F and G Using a Streptavidin-Coated Chip

The assay used biotinylated VAMP construct which consists of GST Human-VAMP-1 (ending in KNLKC-biotin) 5 mg/ml in Hepes (50 mM, pH 7.4). This was diluted with an equal volume of Hepes (50 mM, pH 7.4) buffer containing 50 mM DTT and 50 μM $ZnCl_2$. To 3 μl of the above substrate solution, 12 μl of toxin solution in a buffer such as Hepes (50 mM, pH 7.4) was added and the mixture incubated for 2 hours at 37° C.

Standard toxin solutions were prepared in order to calibrate the assay system. Dilutions of: 0.1, 0.03, 0.01, 0.003, 0.001, 0.0003, 0 μg/ml were prepared in a suitable buffer such as Hepes (50 mM, pH 7.4). These were mixed and incubated with the VAMP substrate as described above.

SELDI chips were labelled with streptavidin as follows. Preactivated PS20 chips (Ciphergen) were place in a humidity chamber and add 3 μl of PBS to each spot (or ammonium bicarbonate, pH8) added. 2 μl of a 0.5-1 mg/ml streptavidin solution in PBS to each spot was the added and the chip incubated for 1 h in the humidity chamber at room temperature or at 4° C. overnight. Residual active sites were blocked by adding 1 μl of 1M ethanolamine (made up in PBS and adjusted to pH 8) and incubating for 30 min. The chip was then washed in a 15 ml falcon tube with 3×5 ml of PBS+0.5% Triton×100, 5 min each and then 2×5 ml of PBS, 5 min. Excess solution was flicked off the chip and the bottom and edges quickly dried. Chips were placed in a humidity chamber and 5 ul PBS added to each spot. Drying was continued around the spots by replacing the 5 μl PBS until the hydrophobic coating was re-established and the 5 μl of PBS sat proud on the spots.

Chips prepared as above were washed with PBS, the buffer removed and 3 μl of each test sample incubations were then added to each spot and incubated for 10 min at RT. Spots were then washed with 2×10 μl Hepes (50 mM, pH 7.4) buffer and 10 μl water. After washing, chips were then air-dried and 2×0.5 μl Energy Absorbing Molecules (alphacyano-4-hydroxy cinnamic acid diluted in 50% acetonitrile and 0.5% trifluroacetic acid to ⅓ saturation) was added and dried.

Chips were then read in a SELDI mass spectrometer (Ciphergen Inc.) Depending on the *botulinum* serotype present, peaks of various masses will be present in the mass spectrum. Approximate masses of the expected peaks are shown below:

peptide product mass for BoNT/B=3039.9
peptide product mass for BoNT/F=4908.9
peptide product mass for BoNT/D=4780.8
peptide product mass for BoNT/G=2390.7

The mass of the peak observed in the spectrum thus confirms and identifies the *botulinum* toxin serotypes present in test samples. The results for a BoNT/B assay are shown in FIG. 3.

Example 5

Assay for *Botulinum* Neurotoxins

Types A and E Using a Streptavidin-Coated Chip

The assay used biotinylated SNAP-25 construct which consists of GST Human-SNAP-25 in which the 4 internal serines have been mutated to cysteine and which a cysteine has been added to the C-terminus and biotinylated (i.e. the protein ends with the sequence LGSGC-biotin). A solution (5 mg/ml in 50 mM Hepes pH 7.4) was diluted with an equal volume of Hepes (50 mM, pH 7.4) buffer containing 50 mM DTT and 50 μM $ZnCl_2$. To 3 μl of the above substrate solution, 12 μl of toxin solution in a buffer such as Hepes (50 mM, pH 7.4) was added and the mixture incubated for 2 hours at 37° C.

In the case of assays for BoNT/C, it is necessary to add positively charged liposomes of synaptosomes to the incubation mixture. For the assays, 1 μl of a 0.2 mg/ml (total protein) solution of rat brain synaptosomes was added.

Standard toxin solutions were prepared in order to calibrate the assay system. Dilutions of: 0.1, 0.03, 0.01, 0.003, 0.001, 0.0003, 0 μg/ml were prepared in a suitable buffer such as Hepes (50 mM, pH 7.4). These were mixed and incubated with the SNAP-25 substrate as described above.

SELDI chips were labelled with streptavidin as follows. Preactivated PS20 chips (Ciphergen) were place in a humidity chamber and add 3 μl of PBS to each spot (or ammonium bicarbonate, pH 8) added. 2 μl of a 0.5-1 mg/ml streptavidin solution in PBS to each spot was the added and the chip incubated for 1 h in the humidity chamber at room temperature or at 4° C. overnight. Residual active sites were blocked by adding 1 μl of 1M ethanolamine (made up in PBS and adjusted to pH 8) and incubating for 30 min. The chip was then washed in a 15 ml falcon tube with 3×5 ml of PBS+0.5% Triton×100, 5 min each and then 2×5 ml of PBS, 5 min. Excess solution was flicked off the chip and the bottom and edges quickly dried. Chips were placed in a humidity chamber and 5 ul PBS added to each spot. Drying was continued around the spots by replacing the 5 μl PBS until the hydrophobic coating was re-established and the 5 μl of PBS sat proud on the spots.

Chips prepared as above were washed with PBS, the buffer removed and 3 μl of each test sample incubations were then added to each spot and incubated for 10 min at RT. Spots were then washed with 2×10 μl Hepes (50 mM, pH 7.4) buffer and 10 μl water. After washing, chips were then air-dried and 2×0.5 μl Energy Absorbing Molecules (alphacyano-4-hydroxy cinnamic acid diluted in 50% acetonitrile and 0.5% trifluroacetic acid to ⅓ saturation) was added and dried.

Chips were then read in a SELDI mass spectrometer (Ciphergen Inc.) Depending on the *botulinum* serotype present, peaks of various masses will be present in the mass spectrum. Approximate masses of the expected peaks are shown below:

peptide product mass for BoNT/A=1548.1
peptide product mass for BoNT/C=1392.0
peptide product mass for BoNT/E=3492.1

The mass of the peak observed in the spectrum thus confirms and identifies the *botulinum* toxin serotypes present in test samples. The results for a BoNT/A assay are shown in FIG. 4.

Example 6

Assay for Anthrax Lethal Factor Using a Streptavidin-Coated Chip

The assay uses a synthetic biotinylated human MAPKK2 peptide which consists of the N-terminal 60 residues and which contains a biotinylated N-terminal cysteine residue (i.e. the protein begins with the sequence biotin-CLARRKP). A solution (0.5 mg/ml in 50 mM Hepes pH 7.4) was diluted with an equal volume of Hepes (50 mM, pH 7.4) buffer containing 50 mM DTT and 50 μM $ZnCl_2$. To 3 μl of the above substrate solution, 12 μl of toxin solution in a buffer such as Hepes (50 mM, pH 7.4) was added and the mixture incubated for 2 hours at 37° C.

Standard toxin solutions were prepared in order to calibrate the assay system. Dilutions of: 0.1, 0.03, 0.01, 0.003, 0.001, 0.0003, 0 μg/ml were prepared in a suitable buffer such as Hepes (50 mM, pH 7.4). These were mixed and incubated with the human MAPKK-2 peptide substrate as described above.

SELDI chips were labelled with streptavidin as follows. Preactivated PS20 chips (Ciphergen) were place in a humidity chamber and add 3 μl of PBS to each spot (or ammonium bicarbonate, pH8) added. 2 μl of a 0.5-1 mg/ml streptavidin solution in PBS to each spot was the added and the chip incubated for 1 h in the humidity chamber at room temperature or at 4° C. overnight. Residual active sites were blocked by adding 1 μl of 1M ethanolamine (made up in PBS and adjusted to pH 8) and incubating for 30 min. The chip was then washed in a 15 ml falcon tube with 3×5 ml of PBS+0.5% Triton×100, 5 min each and then 2×5 ml of PBS, 5 min. Excess solution was flicked off the chip and the bottom and edges quickly dried. Chips were placed in a humidity chamber and 5 ul PBS added to each spot. Drying was continued around the spots by replacing the 5 μl PBS until the hydrophobic coating was re-established and the 5 μl of PBS sat proud on the spots.

Chips prepared as above were washed with PBS, the buffer removed and 3 μl of each test sample incubations were then added to each spot and incubated for 10 min at RT. Spots were then washed with 2×10 μl Hepes (50 mM, pH 7.4) buffer and 10 μl water. After washing, chips were then air-dried and 2×0.5 μl Energy Absorbing Molecules (alphacyano-4-hydroxy cinnamic acid diluted in 50% acetonitrile and 0.5% trifluroacetic acid to ⅓ saturation) was added and dried.

Chips were then read in a SELDI mass spectrometer (Ciphergen Inc.) The approximate mass of the expected peak is shown below:

peptide product mass for anthrax LF=1678.1

The mass of the peak observed in the spectrum thus confirms the presence of anthrax LF in test samples.

Example 7

Assay for *botulinum* Neurotoxin

Type B Using an Antibody-Coated Chip

The assay used a VAMP construct which consists of GST Human-VAMP-1 (ending in KNLK) 5 mg/ml in Hepes (50 mM, pH 7.4). This was diluted with an equal volume of Hepes (50 mM, pH 7.4) buffer containing 50 mM DTT and 50 μM $ZnCl_2$. To 3 μl of the above substrate solution, 12 μl of toxin solution in a buffer such as Hepes (50 mM, pH 7.4) was added and the mixture incubated for 2 hours at 37° C.

Standard toxin solutions were prepared in order to calibrate the assay system. Dilutions of: 0.1, 0.03, 0.01, 0.003, 0.001, 0.0003, 0 μg/ml were prepared in a suitable buffer such as Hepes (50 mM, pH 7.4). These were mixed and incubated with the VAMP substrate as described above.

Purified antibody raised against the sequence CKAASSEF-n terminal was used for the assay procedure. SELDI chips were labelled with antibody as follows. Preactivated PS20 chips (Ciphergen) were place in a humidity chamber and 3 μl of PBS added to each spot (or ammonium bicarbonate, pH 8) added. 2 μl of a 0.5-1 mg/ml antibody solution in PBS to each spot was then added and the chip incubated for 1 h in the humidity chamber at room temperature or at 4° C. overnight. Residual active sites were blocked by adding 1 μl of 1M ethanolamine (made up in PBS and adjusted to pH 8) and incubating for 30 min. The chip was then washed in a 15 ml falcon tube with 3×5 ml of PBS+0.5% Triton×100, 5 min each and then 2×5 ml of PBS, 5 min. Excess solution was flicked off the chip and the bottom and edges quickly dried. Chips were placed in a humidity chamber and 5 μl PBS added to each spot. Drying was continued around the spots by replacing the 5 μl PBS until the hydrophobic coating was re-established and the 5 μl of PBS sat proud on the spots.

Chips prepared as above were washed with PBS, the buffer removed and 3 μl of each test sample incubations were then added to each spot and incubated for 60 min at RT. Spots were then washed with 2×10 μl Hepes (50 mM, pH 7.4) buffer and 10 μl water. After washing, chips were then air-dried and 2×0.5 μl Energy Absorbing Molecules (alphacyano-4-hydroxy cinnamic acid diluted in 50% acetonitrile and 0.5% trifluroacetic acid to ⅓ saturation) was added and dried.

Chips were then read in a SELDI mass spectrometer (Ciphergen Inc.)

Depending on the *botulinum* serotype present, peaks of various masses will be present in the mass spectrum. Approximate mass of the expected peak is shown below:

peptide product mass for BoNT/B=2411.3

The mass of the peak observed in the spectrum thus confirms and identifies the *botulinum* toxin serotypes present in test samples.

The invention claimed is:

1. An assay to detect a metalloprotease in a sample, comprising:
   contacting the sample with a substrate, wherein the metalloprotease reacts with the substrate to form a product comprising a tag; followed by
   selectively binding the tag to a solid phase, wherein the solid phase comprises a binding partner for the tag; and
   measuring the mass of the product, to determine the presence of the metalloprotease in the sample.

2. An assay according to claim 1 wherein the metalloprotease cleaves the substrate to form a product having a lower mass than the substrate.

3. An assay according to claim 1 wherein
   the assay is for detecting whether either or both of a first metalloprotease and a second metalloprotease are present in the sample,
   the first metalloprotease cleaves the substrate to form a first product having a first mass and comprising a first tag, and the second metalloprotease cleaves the substrate to form a second product having a second mass and comprising a second tag,
   wherein the mass of the first product is different from the mass of the second product, and selectively binding the first tag to a solid phase, wherein the solid phase comprises a binding partner for the first tag, and selectively binding the second tag to a solid phase, wherein the solid phase comprises a binding partner for the second tag, and
   measuring the respective masses of the products to determine the presence of the first product, the second product or both the first product and the second product.

4. An assay according to claim 1 wherein the tag comprises a peptide sequence which binds to a hydrophobic surface.

5. An assay according to claim 1 wherein the tag binds to an antibody.

6. An assay according to claim 1 wherein the tag binds to biotin or streptavidin.

7. An assay according to claim 1 wherein the binding partner is specific for the tag.

8. An assay according to claim 7 wherein the binding partner is an antibody specific for the tag.

9. An assay according to claim 1, wherein the substrate is cleaved by *botulinum* toxin, anthrax toxin or anthrax lethal factor.

10. An assay according to claim 1, wherein the substrate comprises:

(a) VAMP, (b) SNAP-25, (c) syntaxin, (d) a fragment of any of (a)-(c) comprising a metalloprotease cleavage site, or (e) a metalloprotease cleavage site.

11. An assay according to claim 1 wherein the substrate comprises:

MAPKK1,

MAPKK2, or a fragment thereof comprising a metalloprotease cleavage site.

12. An assay according to claim 1, further comprising washing the solid phase and detecting product on the solid phase.

13. An assay to detect a plurality of metalloproteases in a sample, comprising:

contacting the sample with at least one substrate, wherein each of the plurality of metalloproteases reacts with a substrate of the at least one substrate to form a respective product comprising a tag, and wherein each product is distinguishable from other respective products by mass; followed by selectively binding the respective tags to a solid phase, wherein the solid phase comprises a binding partner for each respective tag; and measuring the mass of the respective products, to determine the presence of each of the plurality of the metalloprotease in the sample.

14. An assay according to claim 13 wherein each of the plurality of metalloproteases cleaves the substrate to form a corresponding product having a lower mass than the substrate.

15. An assay according to claim 13 wherein the tag comprises a peptide sequence which binds to a hydrophobic surface.

16. An assay according to claim 13 wherein the tag binds to an antibody.

17. An assay according to claim 13 wherein the tag binds to biotin or streptavidin.

18. An assay according to claim 13, wherein the substrate is cleaved by *botulinum* toxin, anthrax toxin or anthrax lethal factor.

19. An assay according to claim 13, wherein the substrate comprises:
 (a) VAMP,
 (b) SNAP-25,
 (c) syntaxin,
 (d) a fragment of any of (a)-(c) comprising a metalloprotease cleavage site, or
 (e) a metalloprotease cleavage site.

20. An assay according to claim 13 wherein the substrate comprises:
 MAPKK1,
 MAPKK2, or
 a fragment thereof comprising a metalloprotease cleavage site.

* * * * *

SEQUENCE LISTING

<160> NUMBER OF SEQ ID NOS: 21

<210> SEQ ID NO 1
<211> LENGTH: 5
<212> TYPE: PRT
<213> ORGANISM: Artificial Sequence
<220> FEATURE:
<223> OTHER INFORMATION: synthetic

<400> SEQUENCE: 1

Lys Asn Leu Lys Cys
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic -continued

```
<400> SEQUENCE: 2

Leu Ala Arg Arg Lys Pro Val Leu Pro
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Trp Trp Lys Asn Leu Lys
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Lys Ala Ala Ser Ser Glu Phe
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Leu Gln Ala Gly Ala Ser Gln
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Arg Ile Asp Glu Ala Asn Gln
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

Gly Leu Met Lys Thr Ala Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8
```

```
Lys Ala Ala Ser Ser Glu Phe
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic

<400> SEQUENCE: 9

Leu Gln Ala Gly Ala Ser Gln
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic

<400> SEQUENCE: 10

Ile Asp Glu Ala Asn Gln Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

Ser Gly Leu Met Lys Thr Ala
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic

<400> SEQUENCE: 12

Val Leu Glu Arg Asp Gln Lys
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic

<400> SEQUENCE: 13

Arg Asp Asp Leu Glu Ser Leu
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic

<400> SEQUENCE: 14
```

```
Gln Asn Arg Gln Ile Asp Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic

<400> SEQUENCE: 15

Ser Asp Ala Lys Glu Met Ile
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic

<400> SEQUENCE: 16

Lys Val Leu Glu Arg Asp Gln
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic

<400> SEQUENCE: 17

Asp Asp Leu Glu Ser Leu Lys
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic

<400> SEQUENCE: 18

Ser Gln Phe Glu Ser Ser Ala
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic

<400> SEQUENCE: 19

Tyr Lys Arg Lys Leu Lys Ala
1               5

<210> SEQ ID NO 20
<211> LENGTH: 7
<212> TYPE: PRT
<213> ORGANISM: Artificial Sequence
```

-continued

```
<220> FEATURE:
<223> OTHER INFORMATION: Synthetic

<400> SEQUENCE: 20

Arg Arg Lys Pro Val Leu Pro
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic

<400> SEQUENCE: 21

Cys Lys Ala Ala Ser Ser Glu Phe
1               5
```